United States Patent [19]

Liu et al.

[11] Patent Number: 4,770,067

[45] Date of Patent: Sep. 13, 1988

[54] METHOD OF MANUFACTURING SURGICAL CUTTING TOOLS FOR THERMALLY AIDED SURGERY

[75] Inventors: Chong-Tan Liu, West Nvack; Yin-Fang Wang, Flushing, both of N.Y.

[73] Assignee: Kollmorgen Corporation, Simsbury, Conn.

[21] Appl. No.: 58,978

[22] Filed: Jun. 8, 1987

[51] Int. Cl.[4] .............................................. B21K 11/02
[52] U.S. Cl. .............................. 76/104 R; 128/303.17
[58] Field of Search ............ 76/101 R, 101 D, 104 R; 128/303.1, 303.17, 303.13, 303.14, 325; 30/140

[56] References Cited

U.S. PATENT DOCUMENTS

| | | | |
|---|---|---|---|
| 3,768,482 | 10/1973 | Shaw | 128/303.1 |
| 3,826,263 | 7/1974 | Cage et al. | 128/303.1 |
| 4,534,347 | 8/1985 | Taylor | 128/303.1 |

Primary Examiner—Roscoe V. Parker
Attorney, Agent, or Firm—Morgan & Finnegan

[57] ABSTRACT

A method of manufacturing a surgical cutting blade having a heating element mounted on the sides thereof which is capable of supplying sufficient thermal energy to cauterize incised tissue and reduce hermorraging of blood vessels at the site of the incision. According to the method, a thermally conductive hardened metallic cutting blade, having a thermal conductivity coefficient of at least 0.6, preferably at least 0.8, which is sufficient to transmit a cauterizing thermal flux from the heating element to the cutting edge at a heating element temperature which does not burn tissue adjacent to the heating element during the incision, is provided with a layer of dielectric insulation adhered directly to the surface of the blade. A heating element pattern is directly adhered to the dielectric insulation layer.

16 Claims, 1 Drawing Sheet

METHOD OF MANUFACTURING SURGICAL CUTTING TOOLS FOR THERMALLY AIDED SURGERY

FIELD OF THE INVENTION

This invention relates to a surgical scalpel suitable for thermally aided surgery. More particularly, this invention relates to a method of manufacturing a surgical scalpel which can be locally heated to supply thermal energy for cauterizing incised tissue in surgical procedures.

BACKGROUND OF THE INVENTION

The use of thermal energy for sealing blood vessels and reducing hemorrhage (hemostasis) in surgery is well known. Various heating means separate from the means used to cut the blood vessels are used during surgery to achieve the hemostasis effect, e.g., auxiliary heating devices as well as lasers. In laser surgery, both argon lasers and carbon dioxide lasers have been used as scalpels for tissue coagulation and hemostasis. The laser scalpels are expensive and bulky, requiring large power supplies and a complex system of heavy mirrors. This makes them inconvenient and cumbersome to use.

Also known are steel blades which are similar to conventional scalpels except that adhered thereto via an adhesive layer is a printed circuit heating element mounted on a polyimide foil. However, the performance of such steel blades is severely limited. The adhesive layer, the polyimide foil thickness and the body of the steel blade severely limit heat transmission from the heating element to the cutting edge of the blade. To achieve a desired amount of heat transmission at the cutting edge of the blades, the temperature of the heating element must be raised to a very high temperature to allow for the loss in heat transmission from the heating element to the cutting edge. However, since the temperature of the heating element must be raised almost 100° C. above the required temperature of the cutting edge to achieve the desired amount of heat transmission at the cutting edge of the blade, the proximity of the heated non-cutting portions of the blade will burn tissue adjacent to the heating element rather than coagulating blood vessels at the cutting edge. Furthermore, the steel cutting edge of the blade will corrode rapidly upon contact with body fluids at such elevated temperatures.

U.S. Pat. No. 3,826,263 to Cage et al. describes a ceramic scalpel blade with a resistance heater emplaced at the cutting edge. The material of the heater preferably has a negative temperature coefficient of resistance. U.S. Pat. No. 3,768,482 to Shaw describes a ceramic blade having a plurality of electrical heating elements disposed on the cutting edges of the blade. Ceramic blades such as those described by Cage et al. and Shaw have not been practical. The ceramic body of the blade was found to be too brittle and thermally non-conductive for practical use. In addition, the heating element(s) was crammed into a very confined area, rendering heating ineffective and making temperature control difficult.

U.S. Pat. No. 4,534,347 to Taylor describes a microwave energy heated scalpel in which the blade is not heated directly. The blade consists of a conducting open loop, and in operation, microwave energy is emitted from the scalpel and absorbed in the tissue being surgically cut to a depth of approximately 10 mm, causing coagulation of blood vessels.

SUMMARY OF THE INVENTION

In one aspect, this invention comprises a method of manufacturing a surgical cutting blade having a heating element mounted on the sides thereof which is capable of supplying sufficient thermal energy to cauterize incised tissue and reduce hemorrhaging of blood vessels at the site of the incision. According to the method, a thermally conductive, hardened metallic cutting blade, having a thermal conductivity coefficient of at least 0.6, preferably at least 0.8, which is sufficient to transmit a cauterizing thermal flux from the heating element to the cutting edge at a heating element temperature which does not burn tissue adjacent to the heating element during the incision, is provided with a layer of dielectric insulation adhered directly to the surface of the blade. Thermal conductivity, as used herein, means the conductivity in Cal/$cm^2$.cm.sec.°C., and typical values are given in ASM METALS REFERENCE BOOK, 2nd Ed., American Society for Metals, Metals Park, Ohio (1983) on pp. 94–95. The layer of insulation is applied thick enough to electrically insulate the blade from the heating element, and thin enough to transmit a cauterizing thermal flux from the heating element to the blade and so that the temperature of the cutting edge is within 30° C., preferably within 10° C., of the temperature of the heating element. A heating element pattern is directly adhered to the dielectric insulation layer.

In another aspect, the invention comprises a method of manufacturing a surgical cutting blade with at least one heating element mounted on the sides thereof capable of supplying thermal energy for cauterizing incised tissue to reduce hemorrhage. The method comprises:

providing an alumina dispersion hardened copper blade, the blade having thermal conductivity sufficient to transmit a cauterizing thermal flux from the heating element to the cutting edge without raising the heating element temperature enough to burn tissue adjacent to the heater;

sharpening the blade;

polishing the sides of the blade sufficient to remove all protrusions greater than about 1 micrometer and smear copper metal over the alumina particles which substantially eliminates the formation of pinholes in a subsequently deposited layer of corrosion resistant metal over the copper blade;

plating an essentially pinhole-free layer of corrosion resistant metal over the copper blade;

adhering a thin layer of dielectric insulation to the corrosive resistant metal layer surface of the blade;

adhering a heating element pattern to the dielectric insulating layer; and applying an insulating coating layer over the heating element.

The layer of corrosion resistant metal must be sufficient to prevent oxidation of the copper blade at cauterizing temperatures. The corrosion resistant metal layer also must be capable of accepting an adherent layer of dielectric insulation. A thin layer of dielectric insulation is adhered directly to the metal layer surface of the blade. The layer of insulation is between about 1 and 20 micrometers thick and thick enough to electrically insulate the blade from the heating element, and thin enough to conduct a cauterizing thermal flux from the heating element to the blade. The layer of insulation does not cover the cutting edge of the blade. The layer of insulation covers at least the surface of the blade underneath the heating element. Preferably the whole blade is covered except the cutting edge. A heating element pattern is formed directly adhered to the dielectric insulation layer and an electrically insulating coating is applied over the heating element, the coating being between about 0.5 and about 100 micrometers thick, and preferably between about 0.5 and 25 micrometers thick. A non-stick coating is applied over the blade to resist adhesion of the blade to tissue at temperatures up to 350° C.

DETAILED DESCRIPTION OF THE INVENTION

Figure 1:
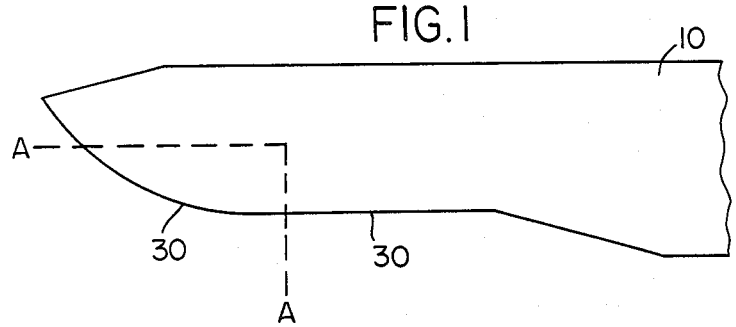
FIG. 1 is a plan view of a surgical cutting blade blank.

The method of manufacturing blades for heated surgical scalpels according to this invention overcomes the aforementioned deficiencies of the prior art. The method of manufacturing surgical scalpels according to the present invention produces a metallic surgical scalpel which is capable of delivering enough thermal energy, through the electric heating element placed on the scalpel body, for simultaneous thermal cutting of tissues and hemostasis of blood vessels. This facilitates not only cutting of tissue but also sterilization at the site of the cutting.

The main body of the scalpel blade is constructed of a highly thermally conductive material such as copper. A highly thermally conductive material is required so that a heat flux can be effectively transmitted from the heating element to the scalpel body and then to the cutting edge. Since highly thermally conductive metals are generally soft, a harder metal such as a dispersion hardened material is used.

Even with the harder compositions of highly thermally conductive metals, a specially developed procedure was found to be necessary to prepare a sharpened cutting edge of the blade. After sharpening, the cutting edge is extremely soft and weak, compared to the steel normally used in scalpels but it then is reinforced by plating a material which is harder than steel over it, such as nickel followed by plating thereover a thin overlayer of chromium. The thickness of a nickel layer should be sufficient to harden the edge of the blade, preferably at least 2 micrometers. The maximum thickness is dependent on the method used for sharpening or stropping the edge after plating. Preferably, the total plating thickness is between 2 and 6 micrometers. The coating for the edge also should protect the cutting edge from the corrosive action of body fluids at elevated temperatures. The corrosion resistance of nickel is poor above 375° C. and a layer of chromium may be added to enhance the corrosion resistance of the blade under operating conditions. The chromium layer should be thick enough to enhance the corrosion resistance, but not thick enough to dull the edge. Usually the chromium layer should be between 0.02 and 2 micrometers thick, and preferably is approximately 0.05 micrometers thick. Other hard materials that are believed to be suitable for reinforcing the cutting edge are coatings of rhodium, titanium nitrides, and carbides.

A properly prepared cutting edge should be as sharp as commercial steel scalpels when used at room temperature, and will require much less force when used at temperatures over 200° C. The cutting edge should remain sharp and free of corrosion after repeated cutting of live tissue at 250°–400° C.

A novel feature of scalpels made by the manufacturing methods of this invention is the intimate contact of the heating element with the metallic scalpel body. In prior art scalpels having one or more heating elements adhered to the blade, the electrical insulators and the bonding adhesives between the heating element(s) and the metallic scalpel body imposed a severe barrier to the thermal flux which limited the heat available at the cutting edge.

In the present invention, thin dielectric insulating films in the order of a few micrometers thick are applied by the methods of this invention. Such dielectric insulating films permit enough heat to be transmitted from the heating element to the metallic body of the blade so that a heating element temperature can be employed which will coagulate blood vessels at the site of the incision but which is insufficient to burn the tissues adjacent to the heating element. The maximum preferred thickness of the insulating film is below about 20 micrometers, more preferably below about 10 micrometers, and most preferably below about 5 micrometers. The minimum preferred thickness is about three times the height of any metallic protrusion from the scalpel body, and should be above at least 1 micrometer, and preferably above about 2 micrometers.

Dielectric films applied to scalpel blanks made of a copper alloy have poor adhesion at elevated temperatures and tend to separate from the blank. Preferably, copper blanks are over coated with an adherent metal layer such as electroplated nickel to prevent loss of adhesion between the dielectric film and the blank. When copper is hardened by dispersing therein alumina particles, the dispersion hardened copper may be used for the blank. However, pinholes will form in the nickel overcoat because the nickel does not deposit on the alumina particles dispersed in the copper matrix. These pinholes will frequently continue through the dielectric layer resulting in short circuits between the heater element and the blank. If a sufficiently thick layer of dielectric film is applied to cover the pinholes, it will cause poor heat transfer from the heater element to the blade. It now has been found that a substantially pinhole free deposit can be achieved by first carefully polishing the dispersion hardened copper blank. Polishing not only levels the surface and removes protrusions, but also smears copper metal over the alumina particles enabling the plating of pinhole free overcoats.

The dielectric layer must be thermally stable up to at least 300° C., preferably up to at least 350° C. and more preferably up to at least 450° C. Thermal stability of the dielectric layer is necessary to maintain adhesion between the heating element and the metallic scalpel body while at the same time maintaining electrical insulation between the heating element and the scalpel cutting edge. Suitable dielectric materials include inorganic materials such as silicon oxides, silicon nitrides and glasses applied by chemical vapor deposition (CVD), sputtering or the like. These inorganic materials are usually applied at thicknesses of 2 to 5 micrometers. Suitable insulating dielectrics also include organic materials such as polyimides and are believed to include fluorocarbon polymers and polyphenylene sulfides. The organic dielectrics are usually applied at thicknesses of 4 to 8 micrometers. Polyimide coatings are conveniently applied by spin coating techniques.

Since the dielectric films are only a few micrometers thick, the surface of the metallic scalpel body must be properly finished so that a continuous, pinhole free and adherent thin dielectric film can be deposited on it. The polishing of the copper surface is described in the examples. Any polishing procedure may be used with copper which smooths protrusions greater than ⅓ the thickness of the dielectric layer, and which covers with copper the alumina particles in the copper blade. If the alumina particles are not covered, pores are formed in the electroplating step and pinholes may result in the dielectric film coat.

The surface of a copper scalpel body preferably is overplated by nickel to improve adhesion of thin film dielectrics and to protect the copper body from surface oxidation at elevated temperature(s). The nickel is deposited over the whole blade surface including the edge and the sides. The thickness of the nickel deposit must be sufficient to prevent oxidation of the copper surface. Usually, the nickel deposit has a thickness of at least one micrometer, and preferably a thickness of at least 2 micrometers. The maximum thickness of nickel deposited must be controlled to maintain the overall thermal conductivity. Since nickel has a thermal conductivity of 0.2 and copper has a thermal conductivity of 0.9, it is preferred to maintain the nickel thickness below 25 micrometers, more preferably below 10 micrometers.

When a silicon oxide or nitride film is applied as the dielectric coating by CVD or sputtering, a nickel surface first has to be deoxidized or activated by ion bombardment.

When organic dielectric films are applied over a nickel plated surface, the wet deposited film should be vacuum degassed before it is heat cured, e.g., in an oven. Suitable organic dielectric materials include self priming polyimide coatings such as PYRALIN TM, and PYRE-ML TM, which are commercially available from E. I. DuPont de Nemours Co., Inc.

The heating element can be applied by depositing an adherent layer of metal over the dielectric film and then etching a resistive heating element pattern on the dielectric film by known photolithographic techniques. A 2 micrometer thick layer of chromium may be sputtered onto a silicon nitride dielectric layer. The heating element pattern then may be printed on the chromium layer with a photoresist and etched to provide the heating element. The dielectric layer must be free of pinholes. If the dielectric layer has pores or pinholes, sputtered chromium will deposit into the pores creating a short circuit from the heating element to the scalpel body. Accordingly, in this invention, the blank is polished and plated to provide a pore-free substrate, because pores in the substrate will form pinholes in the dielectric coating. Conductive inks also are suitable for forming the heating element pattern on organic dielectric layers by serigraphic techniques.

A non-stick coating may be applied to the blade to prevent adhesion of the tissue to the cutting edge. The coating should provide a low surface tension, non-polar surface especially for the cutting edge. It must tolerate heat, abrasion and sterilizing processes. The preferred coating is a fluorinated resin coating or a silicone resin coating. The coating should not be thick enough to dull the blade, and should be at least a monomolecular layer.

EXAMPLE I

Hardened copper scalpel blanks, 10 as shown in FIG. 1, were provided. The blanks had been cut from 0.75 mm thick alumina dispersion strengthened copper, GLIDCOP TM Al-20, commercially available from SCM Metal Products, Cleveland, Ohio. The scalpel blanks had been deburred and ground on a blade edge 30 to a 35° angle.

Figure 2:
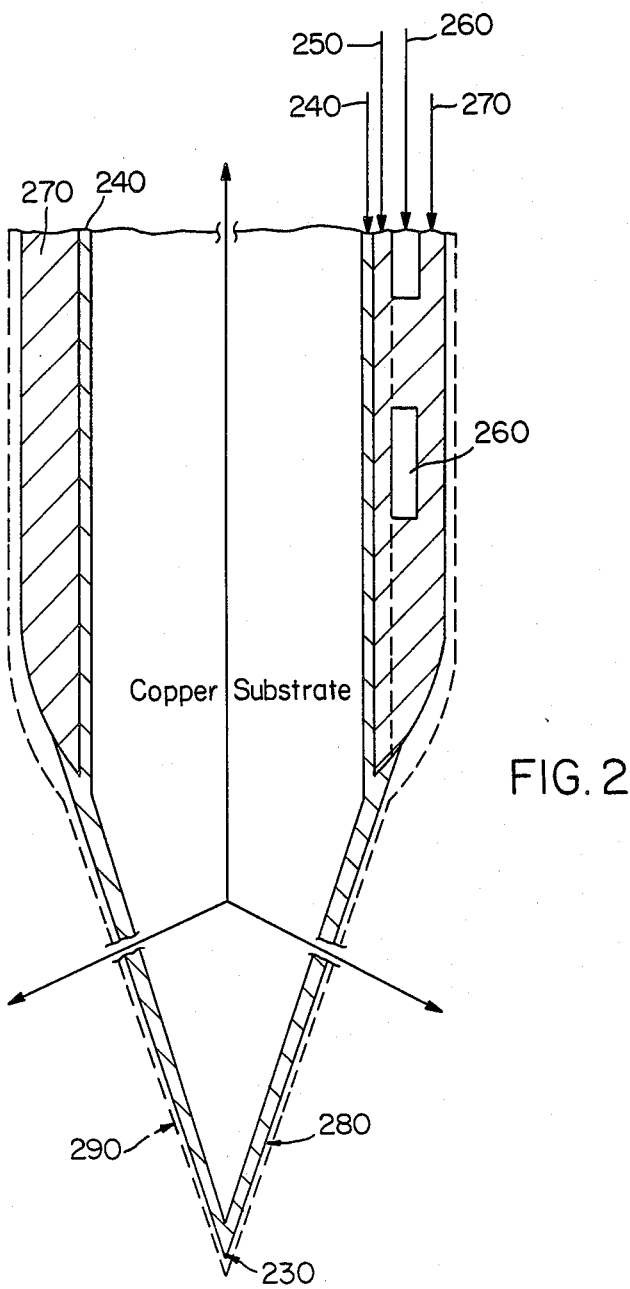
FIG. 2 is a cross section view of a surgical cutting blade produced by the process of this invention.

FIG. 2 is a cross-sectional view of the blade illustrating the sharpened blade edge, 230, and the various coatings applied as detailed below.

The scalpel blanks provided were solvent degreased with butanone before further processing.

The blanks were polished on the sides where the heating element would be placed using a Buehler Metallograph with 400 grit silicon carbide abrasive paper to remove scratches. This was followed by polishing with 600 grit silicon carbide abrasive paper, and a final polish using an alpha alumina slurry have particles sized 0.3 micrometers. Polishing removed all protrusions greater than 0.3 micrometers from the copper surface. Polishing also smeared a conductive copper layer over the dispersed alumina particles on the surface of the scalpel blank.

The surfaces of the scalpels were covered with lacquer to protect the polished finish during the next operation. The lacquer was not applied to the blade edges. The blade edges 230 were stropped with a fine buffing compound on a 75 mm diameter leather wheel rotating no faster than 100 rpm. Then, the lacquer was removed with butanone.

The scalpels were ultrasonically cleaned in butanone, then cleaned with a hot alkaline cleaner, rinsed, dipped in dilute sulfuric acid and electroplated with a nickel deposit 2 micrometers thick. The nickel deposit is shown in FIG. 2 as 240. The nickel plating solution was an aqueous solution which had the following composition and operating conditions:

$NiSO_4.6H_2O$: 170 g/l
$NiCl_2.6H_2O$: 45 g/l
$H_3PO_3$: 20 g/l
$H_3PO_4(85\%)$: 10 g/l
Temperature: 75°–85° C.
Current Density: 3.5 A/dm$^2$ A polyamic acid lacquer coating (PYRALIN TM PI2570D from E. I. DuPont de Nemours & Co. Inc., Wilmington, Del.) was applied to both sides of the blade surface. The lacquer coating was degassed in a vacuum cell to eliminate air bubbles. The coated blades were heated to 80° C. while spinning to achieve a uniform coating approximately 5 micrometers thick. The dried lacquer was removed from the blade edge 230 with N-methyl pyrrolidone and butanone. The lacquer coated scalpels were heated to 150° C. for 15 minutes and then to 350° C. for 30 minutes to convert the lacquer to a heat resistant polyimide coating 250 shown in FIG. 2.

Heating elements 260, were printed over the polyimide coating on the polished side of the blade. The heating elements 260 were printed by serigraphic techniques using a conductive ink consisting of silver pigments in a high temperature polymer vehicle (CONDUCTIVE COMPOSITION #19910 TM commercially available from Electro-Science Laboratories, Inc., King of Prussia, Pa.). The conductive ink was cured by first drying at 125° C. for 10 minutes, then heating at 165° C. for 15 minutes and then heating at 350° C. for 60 minutes.

The heating elements were coated with a protective cover coat by spin coating with a polyamic acid lacquer (PYRALIN PI2570D) 0.5 micrometers thick. Excess polymer was wiped off the edge of the blade with solvent, and the lacquer was cured to a polyimide coating 270, shown in FIG. 2, by baking at 350° C. for 30 minutes.

The blade edges, 230, were carefully stropped with a fine buffing compound on a 75 mm diameter leather wheel rotating about 100 rpm. After stropping, the blades were ultrasonically cleaned twice using butanone, soaked in a hot alkaline cleaner (OAKITE TM 90) at 75° C., rinsed, soaked in an aqueous 10% sulfuric acid solution, and then the cutting edges were electroplated with a layer of nickel to a thickness of approximately 2 micrometers. The blade edges again were carefully stropped, ultrasonically cleaned and electroplated with a layer of chromium, 280, to a thickness of approximately 0.05 micrometers.

A non-stick coating, 290, (VYDAX TM 1000 from E. I. DuPont de Nemours and Co., Inc.) was applied to the scalpels by spray coating, and cured at 350° C. for 10 minutes. The maximum thickness of the non-stick coating thickness was 10 micrometers on the sides of the blade and over the heating element. The non-stick coating thins down at the sharp edge of the blade and is believed to be 1 micrometer thick at the edge. Scalpels prepared according to procedures shown in the method were tested on live dogs. About 30 cuts of ½ inch deep were performed with each tested blade. Complete hemostasis and thermal-aided cutting were observed in the range of 200°-400° C. Temperature response, controlled by the resistance sensing device, was excellent over the entire range from room temperature to 400° C.

EXAMPLE II

Scalpel blanks with the blade edges ground and deburred are provided as in Example I. The blanks are degreased and polished as in Example I to remove protrusions and to smear copper over the aluminum particles dispersed in the blank. The edges are stropped and the blanks are electroplated with nickel as in Example I.

A liquid photoresist is applied to the blanks by spin coating. The photoresist is exposed and developed to leave a protective layer of photoresist on the edge of the scalpel blades and no resist on the sides of the blades where the heating element is to be formed.

The scalpel blades are inserted in a vacuum chamber and cleaned by ion sputtering with an inert gas. Cleaning is essential to ensure good adhesion of the subsequent layers on the nickel plated blades. Low pressure silane and ammonia are introduced into the chamber and a silicon nitride dielectric insulating layer is deposited to a thickness of 5 micrometers on the blades by plasma enhanced chemical vapor deposition at 300° C. This is followed by sputter coating a chromium layer 0.2 micrometers thick.

The photoresist is stripped from the blade edges with solvent, lifting off the portion of the layers of silicon nitride and chromium that had been applied to the blade edges. A fresh photoresist coating is applied to the blades and exposed and developed, leaving a protective layer of photoresist on the blades edges, and outlining the desired heating element conductive pattern.

The blades are placed in a vacuum chamber, cleaned by inert gas ion sputtering, and sputter coated with a layer of gold to a thickness of 3 micrometers.

The photoresist is stripped with solvent leaving exposed the blade edges and the portion of the chromium layer outlining the gold plated conductive pattern. The blade edges are covered with an alkaline strippable resist, and then the exposed chromium is etched away using a solution of 350 ml hydrochloric acid, 150 ml sulfuric acid and 500 ml water. This exposes the silicon nitride insulation outlining the gold conductive pattern.

The resist covering the blade edges is stripped and a protective lacquer is applied over the conductive pattern. The edges are stropped on a 75 mm diameter leather wheel, cleaned, and electroplated with a layer of nickel to a thickness of 2 micrometers. The blade edges again are stropped and electroplated with a chromium flash.

The protective layer is removed and a 0.5 micrometer thick polyimide coating is applied over the conductive pattern of the heating elements as in Example I. This was followed by application of a non-stick coating as in Example I.

EXAMPLE III

Example I is repeated except that the insulating dielectric layer is 12 micrometers thick and is made by application of a polyamic lacquer, PYRE-ML RC-5019 from E. I. DuPont deNemours & Co., Inc. and the cure of the lacquer is at 300° C. for 15 minutes. PYRE-ML RC-5019 also is used as the cover coating.

The blades are tested as in Example 1 except the operating temperatures range from 120° C. to 300° C. These blades give results comparable to Example I when used for thermally assisted surgery.

What is claimed is:

1. A method of manufacturing a surgical cutting blade with at least one heating element mounted on the sides thereof capable of supplying thermal energy for cauterizing incised tissue to reduce hemorrhage comprising:

providing an alumina dispersion hardened copper blade, the blade having a thermal conductivity coefficient >0.6 which is sufficient to pass a cauterizing thermal flux from the heating element to the cutting edge, so that a heating element temperature can be employed which does not burn tissue adjacent to the heating element during the incision but provides a cutting edge temperature sufficient for cauterizing incised tissue to reduce hemorrhage;

sharpening the blade;

polishing the sides of the blade sufficiently to remove all protrusions greater than about 1 micrometer and smear copper metal over the alumina particles such that the formation of pinholes will be essentially eliminated in the layer of corrosion resistant metal subsequently deposited over the copper blade;

plating a layer of corrosion resistant metal over the copper blade, the layer of metal preventing oxidation of the copper blade at cauterizing temperatures and being capable of accepting an adherent layer of dielectric insulation;

adhering a layer of dielectric insulation to the metal layer surface of the blade, the layer of insulation being about 1 and about 20 micrometers thick and thick enough to electrically insulate the blade from the heating element, and thin enough to transmit a cauterizing thermal flux from the heating element to the blade so that the temperature of the cutting edge is within 30° C. of the temperature of the heating element, the layer of insulation not covering the cutting edge;

adhering a heating element pattern onto the dielectric insulation layer;

applying an electrically insulating coating over the heating element, the coating being between about 0.5 and about 100 micrometers thick; and applying over the blade a non-stick coating having a thickness which is sufficient to reduce adhesion of the blade to tissue at temperatures up to 350° C.

2. The method of claim 1 wherein the corrosion resistant metal layer which is plated over the blade comprises a layer of nickel containing an overlayer of chromium.

3. The method of claim 1 wherein the dielectric insulation layer adhered to the metal layer surface of the blade is between about 2 and 10 micrometers thick.

4. The method of claim 1 wherein the dielectric insulation layer adhered to the metal layer surface of the blade has thermal stability up to at least 450° C. and is selected from the group consisting of fluorocarbon polymers, polyimides, polyphenylene sulfides, silicon nitrides, silicon dioxides and glasses and mixtures thereof.

5. The method of claim 4 wherein the material is applied to the blade by chemical vapor deposition.

6. The method of claim 4 wherein the material is applied to the blade by spin coating.

7. The method of claim 4 wherein the material is applied to the blade by spray coating.

8. The method of claim 1 wherein the layer of dielectric insulation is applied about 5 micrometers thick.

9. The method of claim 1 further comprising applying a hard, corrosion resistant layer over the cutting edge of the blade to a thickness between about 2 and 5 micrometers.

10. The method of claim 9 wherein the layer is applied by plating nickel and chromium over the cutting edge of the blade.

11. The method of claim 1 wherein the heating element is formed by vacuum sputtering techniques.

12. The method of claim 1 wherein the heating element is formed by silk screen printing of conductive inks.

13. The method of claim 12 wherein the conductive particles in the ink have a minimum diameter greater than the maximum pore size of the dielectric insulation layer.

14. The method of claim 1 wherein the dielectric layer is a material selected from the group consisting of silicon nitrides, silicon dioxides and glasses and mixtures thereof, and the heating element is formed by deposition of about 2 micrometers of chromium and etching a heating element pattern in the chromium layer.

15. The method of claim 14 wherein the dielectric layer comprises a material selected from the group consisting of fluorocarbon polymers, polyimides and polyphenylene sulfides and combinations thereof, and the heating element is formed by screen printing a conductive ink.

16. A method of manufacturing a surgical cutting blade having a body, a cutting edge and a heating element mounted on the sides thereof capable of supplying thermal energy to the cutting edge sufficient to cauterize incised tissue and reduce hemorrhaging of blood vessels at the site of the incision, said method comprising the steps of:

providing a thermally conductive, hardened metallic cutting blade, the blade having a thermal conductivity coefficient >0.6 which is sufficient to transmit a cauterizing thermal flux from the heating element to the cutting edge at a heating element temperature which does not burn tissue adjacent to the heating element during the incision;

adhering a layer of dielectric insulation directly to the surface of the blade, the layer of insulation being thick enough to electrically insulate the blade from the heating element, and thin enough to transmit a cauterizing thermal flux from the heating element to the blade and so that the temperature of the cutting edge is within 30° C. of the heating element;

adhering a heating element pattern to the dielectric insulation layer.

* * * * *